United States Patent [19]

Skinner et al.

[11] 4,243,752

[45] Jan. 6, 1981

[54] **PRODUCTION OF INCREASED YIELDS OF CELLULOLYTIC ENZYMES FROM *THIELAVIA TERRESTRIS* AND SEPARATING METHODS THEREFOR**

[75] Inventors: Wilfred A. Skinner, Portola Valley, Calif.; Shigeyuki Takenishi, Nara, Japan

[73] Assignee: SRI International, Menlo Park, Calif.

[21] Appl. No.: 28,500

[22] Filed: Apr. 9, 1979

[51] Int. Cl.$^3$ .............................................. C12N 9/42
[52] U.S. Cl. .................................. 435/209; 435/816; 435/911
[58] Field of Search ...................... 435/209, 816, 911

[56] References Cited

U.S. PATENT DOCUMENTS

| | | | |
|---|---|---|---|
| 3,734,831 | 5/1973 | Hulme | 435/209 |
| 4,081,328 | 3/1978 | Skinner et al. | 435/209 |
| 4,106,989 | 8/1978 | Komura et al. | 435/209 |

*Primary Examiner*—Lionel M. Shapiro
*Attorney, Agent, or Firm*—Donovan J. De Witt

[57] ABSTRACT

Increased yields of the cellulolytic enzymes from *Thielavia terrestris* are effected by novel separatory methods for the produced enzymes as well as the enhancement of the production of one of the enzymes, namely β-glucosidase, by the addition of glycerol to the media. Further, since the β-glucosidase is responsible for glucose production from cellulose, a method is provided wherein the separated β-glucosidase can be employed as, for example, on a fixed support in a position to receive concentrated streams of partially converted cellulosic materials, thereby leading to enhanced glucose production.

4 Claims, 6 Drawing Figures

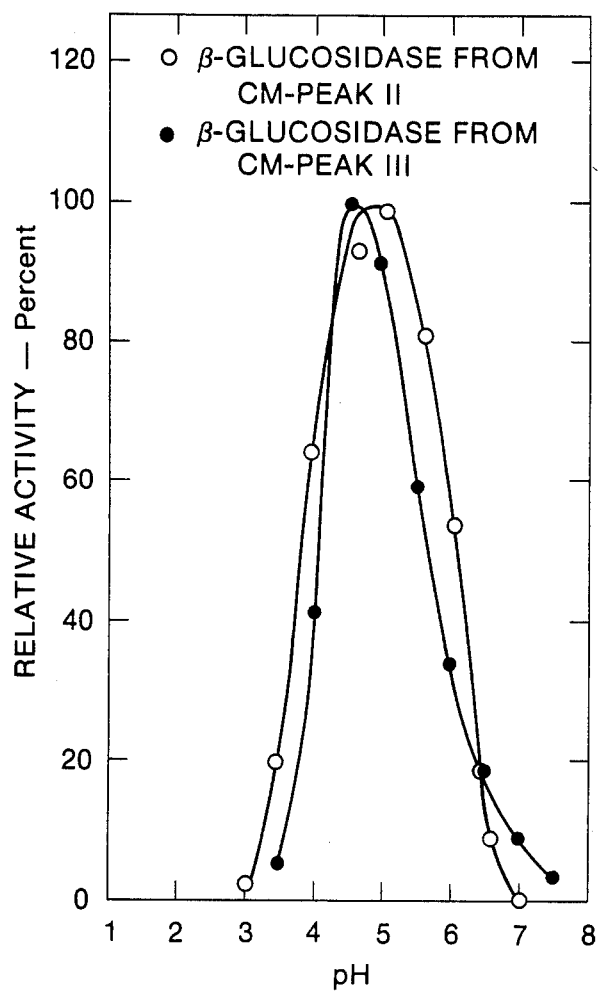
Figure 1 EFFECT OF pH ON ENZYME ACTIVITY OF TWO β-GLUCOSIDASES

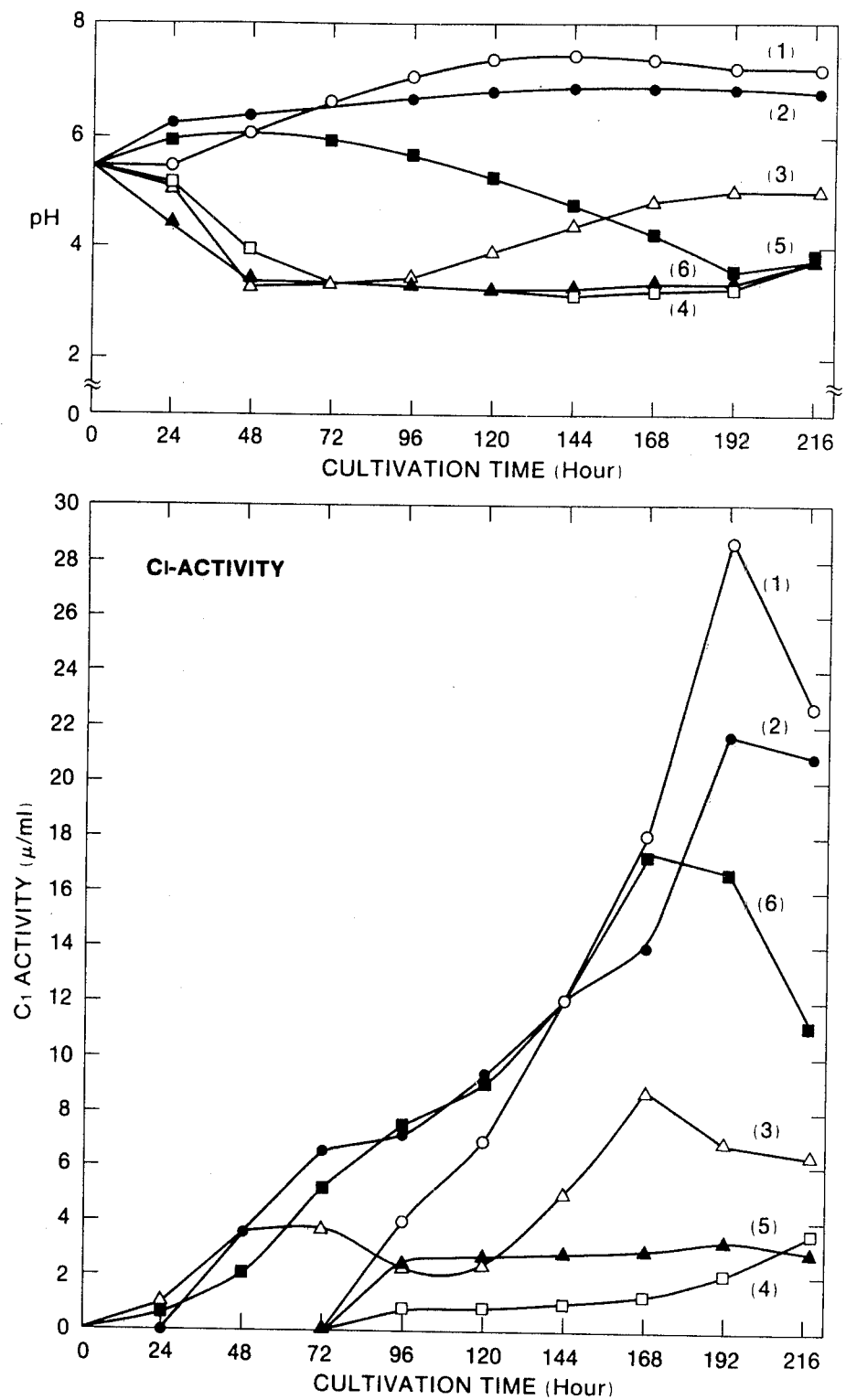
Figure 2 CHANGES IN pH AND $C_1$ ENZYME ACTIVITY, WITH CULTIVATION TIME WITH VARIABLE MEDIA

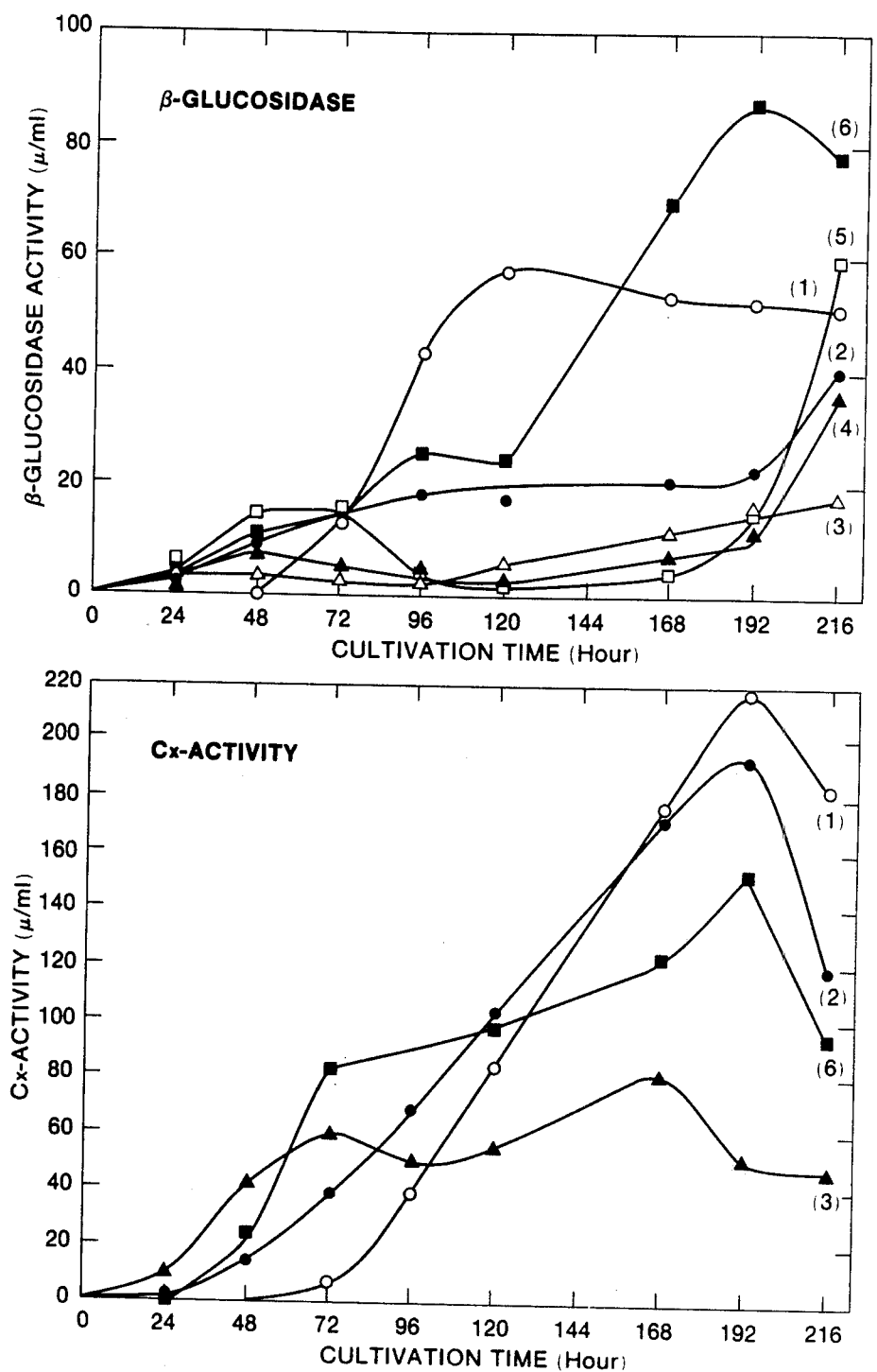
Figure 3 EFFECT OF MEDIA CHANGE AND CULTIVATION TIME ON β-GLUCOSIDASE AND Cx ENZYME ACTIVITIES

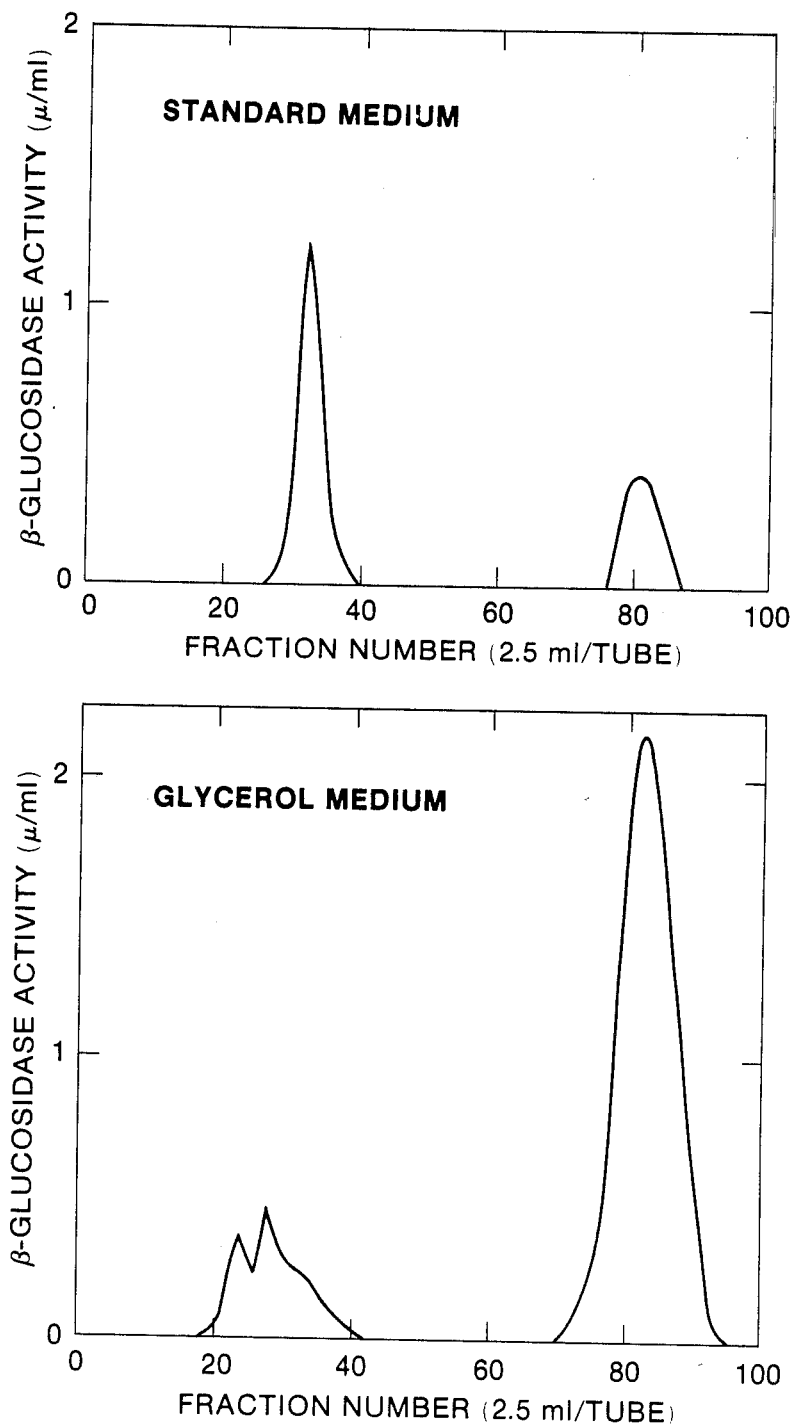
Figure 4 GEL FILTRATION SEPARATION OF β-GLUCOSIDASE ENZYMES FROM STANDARD AND GLYCEROL CONTAINING MEDIA

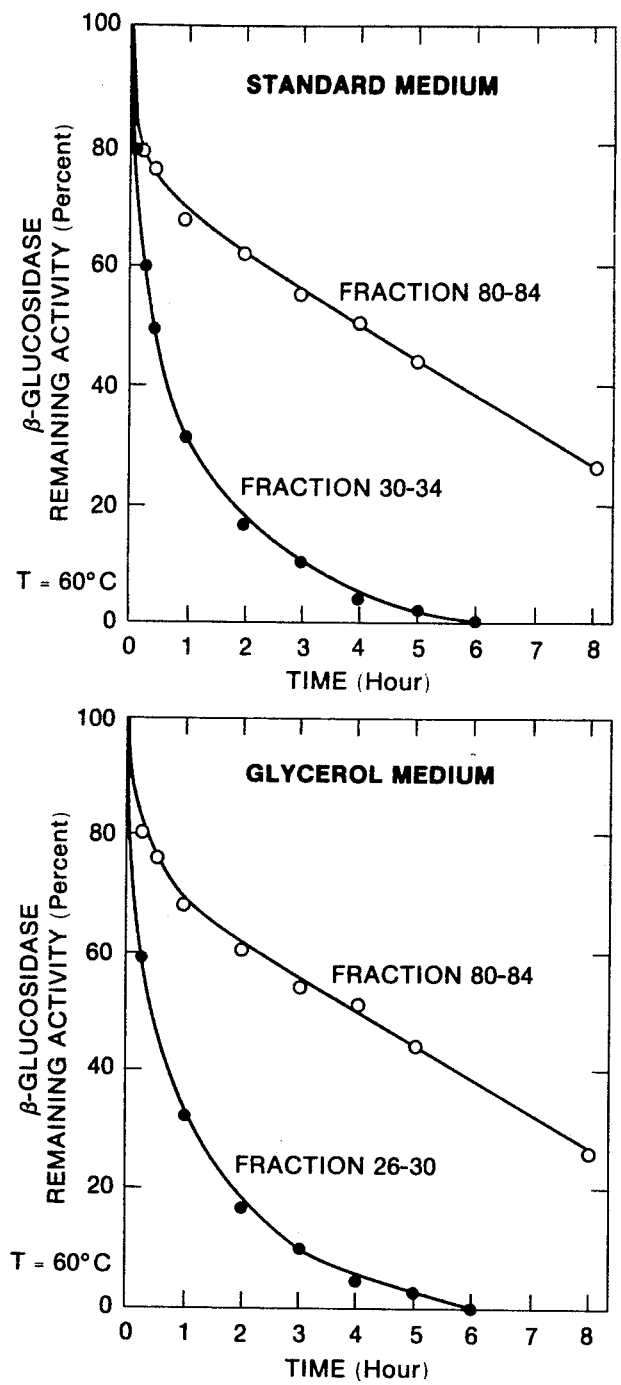
Figure 5 THERMAL STABILITY OF β-GLUCOSIDASE ENZYMES ISOLATED FROM STANDARD AND GLYCEROL CONTAINING MEDIA

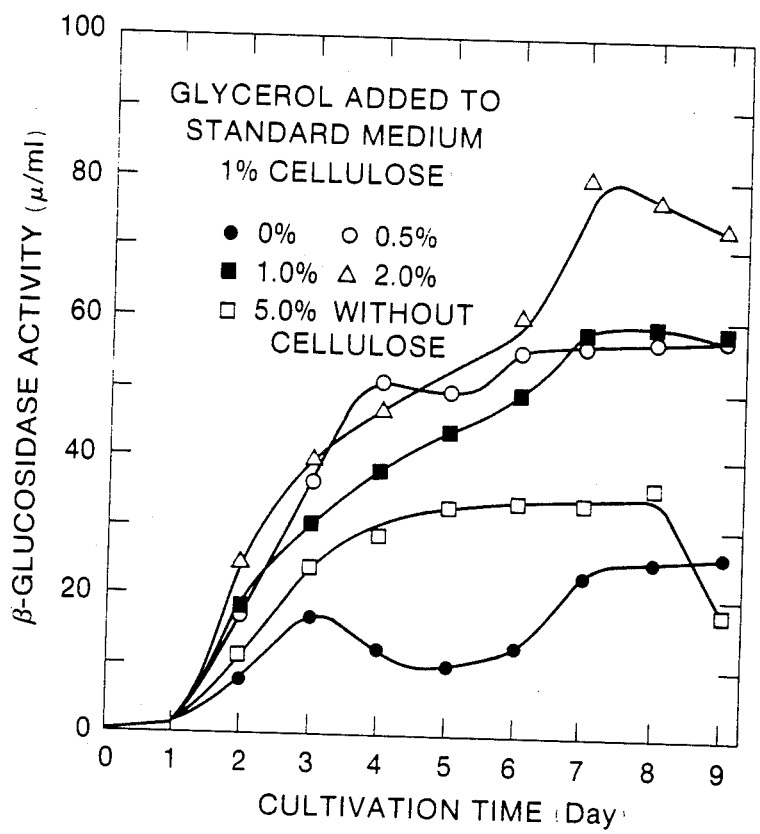
Figure 6 EFFECT OF GLYCEROL IN MEDIA ON PRODUCTION OF β-GLUCOSIDASE ENZYMES

PRODUCTION OF INCREASED YIELDS OF CELLULOLYTIC ENZYMES FROM *THIELAVIA TERRESTRIS* AND SEPARATING METHODS THEREFOR

SUMMARY OF THE INVENTION

It has now been discovered that the cellulase activity of the mixed enzymes derived from *Thielavia terrestris* as disclosed in U.S. Pat. No. 4,081,328 can be purified and/or separated to enhance said activity. Further, it has unexpectedly been discovered that, contrary to previous reports covering other organisms producing cellulases wherein glycerol is reported to have an inhibitory effect, no such results are obtained when using *Thielavia terrestris* as the cellulase producing organism. Thus, it has been found that by using the latter organism in conjunction with glycerol it becomes possible to increase the yield of $\beta$-glucosidase about five-fold while not decreasing the $C_1/C_x$ cellulase production.

The following articles treat of the repression of cellulase production by glycerol or glucose when employing organisms other than *Thielavia terrestris*:

Mandels, 1975, *Growth and Cellulase Production by Trichoderma*, pp. 81-109. In Bailey et al, *Symposium on the Enzymatic Hydrolysis of Cellulose*, The Finnish National Fund for Research and Development (SITRA), Helsinki, Finland.

Nisizawa et al, 1972, *Catabolite Repression of Cellulase Fermentation in Trichoderma Viride, J. Biol. Chem.* 71, 999-1007.

Montenecourt et al, 1977, *Preparation of Mutants of Trichodermia reisei with Enhanced Cellulase Production*, Appl. and Env. Microbiol., 34, No. 6, 777-782. This study that 5% glycerol repressed cellulase production and also vastly reduced the amount of extra cellular protein synthesized relative to that secreted when cellulose was the sole carbon source.

DISCLOSURE OF THE INVENTION

Contrary to the indications of the prior art studies, as noted above, it has now been found that when glycerol is added to a *Thielavia terrestris*-containing media used to produce cellulases from said organism, there is unexpectedly obtained an increase in the production of said enzymes. It was further found that production of $C_1$ and $C_x$ enzyme activities were not affected by the addition of the glycerol, but that the production of $\beta$-glucosidase activities could be increased above five-fold. Further, by gel filtration—separation techniques, it was found that in the presence of glycerol the composition of the $\beta$-glucosidases changed from that found in the standard media per se. Thus, the proportion of the more heat-stable of the $\beta$-glucosidase enzymes was increased, relative to the less heat stable ones, an important practical result, since heat stability is an extremely desirable property in order to increase yields of glucose prepared from cellulosic materials by operating at higher temperatures. Further, stability to heat by the cellulases makes it possible, by heating the system, to continue the enzymatic activity attributable to said cellulases while simultaneously effecting the destruction of relatively heat sensitive, undesirable enzymes that may be present. Exemplary undesirable enzymes that can be eliminated in this fashion, while preserving the valuable cellulases, are those which cause unwanted effects such as protein hydrolysis, various deaminations, hydrolysis of lipids and the like.

With respect to the amount of glycerol that may be added to the media with positive and beneficial effects in increasing the yield of $\beta$-glucosidases, it is found that as little as about 0.5 wt/% is effective, while amounts up to about 5 wt/% may be employed to advantage. Thus, this phenomenon is a clearly unexpected discovery since, as indicated, it is well known to the prior art that the production of cellulolytic enzymes of e.g. Trichoderma, is catabolite repressed with glucose and glycerol.

To demonstrate this unexpected effect of glucose and glycerol on the production of cellulolytic enzymes with *Thielavia terrestris*, a number of studies were performed using the various media compositions, as indicated:

(A) Medium composition (Avicel 105 is cellulose powder and CSL is corn steep liquor).

| No. | Basal Medium* | Avicel 105 | Peptone | CSL | Glucose | Cellobiose | Glycerol |
|---|---|---|---|---|---|---|---|
| 1 | 100 ml | 1 g | 2 g | 2 g | | | |
| 2 | 100 ml | 1 g | 0.5 g | 0.5 g | | | |
| 3 | 100 ml | 1 g | 0.1 g | 0.1 g | | | |
| 4 | 100 ml | 1 g | 0.5 g | 0.5 g | 5 g | | |
| 5 | 100 ml | 1 g | 0.5 g | 0.5 g | | 5 g | |
| 6 | 100 ml | 1 g | 0.5 g | 0.5 g | | | 5 g |

*Basal medium: $KH_2PO_4$ 6.8 g/l, $(NH_4)_2SO_4$ 1.3 g/l, $MgCO_4$ $7H_2O$ 0.5 g/l, $CaCl_2$ 0.2 g/l, trace element solution 2 ml/l.

(B) Cultivation: Preculture was prepared by transferring a small amount of mycelium from slant to a 250 ml flask containing 100 ml of the medium No. 2. The flask was kept at 48° C. for 48 hr on the rotary shaker. The main culture was started by transferring 2 ml of the medium from the preculture to a 250 ml flask containing 100 ml of the medium. The cultivation was carried out on a rotary shaker at 48° C.

(C) Result:

As shown in the Figures, the production of cellulolytic enzymes of *Thielavia terrestris* is suppressed by glucose, like that of Trichoderma. However, glycerol did not have any effect on the production of $C_1$ (filter paper activity) and $C_x$-activity. *Thielavia terrestris* produced about five times the $\beta$-glucosidase in the medium containing 5% glycerol, compared with the production in the standard medium (No. 2) (compare U.S. Pat. No. 4,081,328). Also, it was found that with gel-filtration there are differences in the composition of the $\beta$-glucosidases obtained from the standard medium vis-a-vis the glycerol containing medium.

Optimum temperature for cellulase activity was determined to be about 60° C. These activities can be measured by means of the following assay methods. The thermostable cellulases produced by *Thielavia terrestris* produces 10-12 units of filter paper activity, 25-30 units of aryl $\beta$-glucosidase and 80-90 units of CMC-ase in 1 ml of centrifugate of the culture liquid.

Enzyme Assay

1. Filter paper activity

There was employed a 100 mg strip of Whatman No. 1 filter paper (1×12 cm) as substrate. The assay mixture in a test tube (16×150 mm) is composed of 1 ml of 0.5 M acetate buffer, pH 5.0, a strip of filter paper which was folded just like bellows, and 1 ml of diluted enzyme solution. The mixture is kept for one hour in the water bath (60° C.). After incubation, 2 ml of dinitrosalicylic acid reagent is added to the assay mixture and produced reducing sugars are determined by DNS method and calculated as glucose equivalent. One unit of filter paper activity is defined as the amount of enzyme that produces 1 mg of glucose equivalent reducing sugars under the conditions described above.

2. CMC-ase

The assay mixture is composed of 1 ml of 1% of carboxymethyl cellulose (SIGMA, Product No. C-8758) containing 0.5 M acetate buffer, pH 5.0, and 1 ml of diluted enzyme solution. The mixture is kept for 30 min at 60° C. After incubation, 2 ml of dinitrosalicylic acid reagent is added to the mixture and produced reducing sugars are measured by DNS method and calculated as glucose equivalent. One unit of CMC-ase is defined as the amount of enzyme that produces 1 mg of glucose equivalent reducing sugars under the conditions described above.

3. Aryl β-Glucosidase o-Nitrophenyl β-D-glucopyranoside as used as substrate.

The assay mixture contained 0.5 ml of 10 mm o-nitrophenyl β-D-glucopyranoside, 0.5 ml of 0.5 M acetate buffer, pH 5.0, and 1 ml of diluted enzyme solution. After incubation for 30 min at 60° C., 2 ml of 0.2 M sodium carbonate was added to the mixture; o-nitrophenol released was measured by the absorbance at b 410 nm. One unit of aryl β-glucosidase is defined as the amount of enzyme that produces 1μ mole of o-nitrophenol under the conditions described above.

Using these assay methods to follow fractionation procedures, we have separated the $C_1$, $C_X$, and β-glucosidases from one another by the following scheme:

glucosidases isolated from each other. FIG. 1 illustrates the effect of pH on the activity of two β-glucosidases.

Using the fractionation scheme outlined previously with Bio-Gel P-150, the β-glucosidases were separated into two homogeneous fractions by elution with 0.1 M sodium acetate buffer, pH 5.0. The flow rate was 27 ml/hr and 7 ml fractions were collected.

The data relative to the unexpected discovery that, contrary to previous reports with other organisms producing cellulase, glycerol with *Thielavia terrestris* was able to increase the yield of β-glucosidase enzyme above five-fold, rather than inhibit its production while that of the $C_1/C_X$ production was unchanged, are indicated in FIGS. 2, 3, 4 and 5.

The composition of the β-glucosidases was also changed in the presence of glycerol from that found with the standard media (FIG. 4). The more heat-stable of the β-glucosidase enzymes (FIG. 5) was increased relative to the less heat-stable ones, an important practical result, as heat stability is an important property, in order to increase yields of glucose from cellulosic materials.

Investigation of the effect of glycerol concentration in the media on the yield of β-glucosidases indicated that as little as 0.5% glycerol had a positive effect.

FIG. 2 illustrates changes in pH and $C_1$ activity with cultivation time using variable media. Using the media described in Example No. 1, the effects on $C_1$ activity and pH changes with cultivation time are depicted. These data show that glucose suppressed production of cellulase enzymes, but that glycerol had no effect on $C_1$ or $C_X$ activities, though it increased the yield of β-glucosidase.

FIG. 3 shows the effects of the changing media on β-glucosidase and $C_X$ activities.

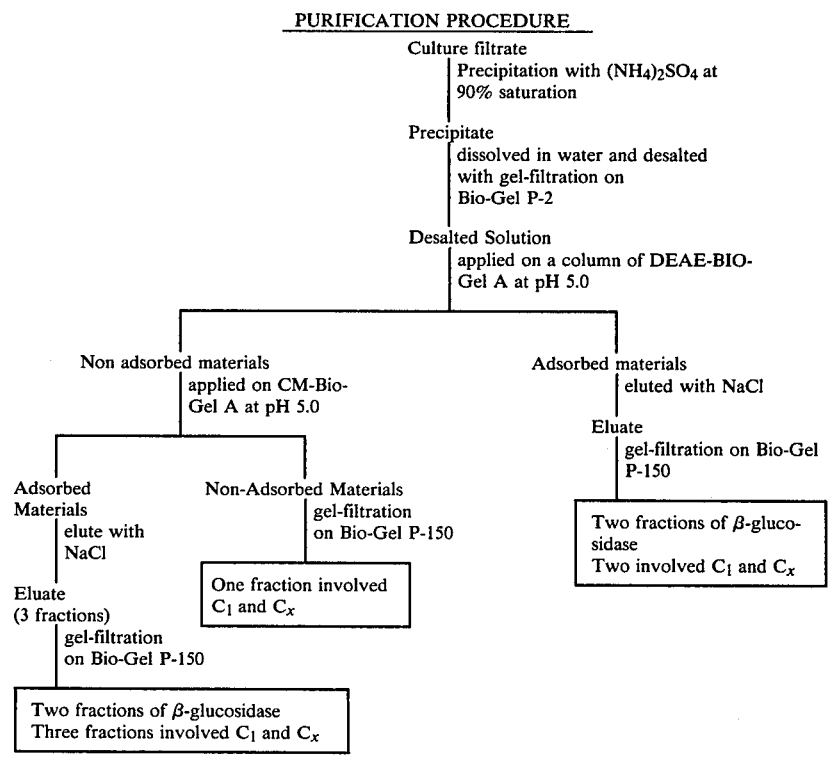

PURIFICATION PROCEDURE

As indicated in FIG. 1, separation of these enzymes was successful to a degree with two homogeneous β-

FIG. 4 depicts the results of the gel filtration separation of β-glucosidases from standard media and glycerol containing media, indicating how the yields of the two different β-glucosidases are influenced by addition of glycerol to the standard media. The fraction around No. 80 is increased with the addition of glycerol and this is the more heat-stable of the two β-glucosidases purified.

FIG. 5 shows that production of the more stable β-glucosidase is favored when glycerol is added to the medium.

FIG. 6 shows the effect on glycerol concentration on the production of β-glucosidases. It is evident that the yields are dramatically increased when glycerol is added to the standard medium. Even an amount as low as about 0.5% glycerol addition has a positive effect on enzymal yield from cellulose as a substrate.

The importance of having easily accessible sources of glucose has been outlined above and in U.S. Pat. No. 4,081,328.

By the novel procedures of the invention herein, significantly larger proportions of β-glucosidase are now able to be produced from *Thielavia terrestris*. Further, by the novel separatory procedures disclosed, purification and/or separation of the β-glucosidase is made possible. The separated β-glucosidase can now be employed in an efficient and economical manner to convert cellulosic materials, e.g., partially converted cellulosic materials leading to enhanced glucose production. In a specific aspect thereof, the β-glucosidase can be employed on a fixed support or trapped in a polymer matrix in a position to receive concentrated streams of the cellulosic raw material for efficient conversion thereof to the desired glucose.

The invention has been described in detail with particular reference to the preferred embodiment thereof, but it will be understood that variations and modifications within the spirit and scope of the invention may occur to those skilled in the art to which the invention pertains.

We claim:

1. A method for increasing the yields of cellulase enzymes from *Thielavia terrestris* whereby there is added from about 0.5% to about 5% of glycerol to the standard media employed to produce said cellulase enzymes.

2. A method according to claim 1 wherein the cellulase enzyme produced in increased yield is the more thermally stable β-glucosidase.

3. The method of claim 1 wherein the enzymes produced are purified and separated by (1) filtering the media culture, (2) precipitating with ammonium sulfate saturated solution, (3) solubilizing and then desalting with gel-filtration, (4) eluting with sodium chloride, (5) further subjecting said eluates to gel-filtration to obtain various separated fractions of β-glucosidase, and $C_1$ and $C_X$ enzyme activities.

4. The method of claim 3 wherein the separated β-glucosidase is further employed for conversion of cellulosic materials to glucose wherein a stream of said cellulosic material is received by the β-glucosidase on a fixed support or trapped in a polymer matrix.

* * * * *